US00PP16476P3

(12) United States Plant Patent
Lyrene

(10) Patent No.: US PP16,476 P3
(45) Date of Patent: Apr. 25, 2006

(54) BLUEBERRY PLANT CALLED 'ABUNDANCE'

(50) Latin Name: *Vaccinium corymbosum*
Varietal Denomination: Abundance

(75) Inventor: Paul M. Lyrene, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 214 days.

(21) Appl. No.: 10/871,999

(22) Filed: Jun. 21, 2004

(65) Prior Publication Data

US 2005/0283865 P1 Dec. 22, 2005

(51) Int. Cl.
*A01H 5/00* (2006.01)

(52) U.S. Cl. ..... Plt./157

(58) Field of Classification Search ..... Plt./157
See application file for complete search history.

*Primary Examiner*—Anne Marie Grunberg
*Assistant Examiner*—Annette H Para

(57) ABSTRACT

A new and distinct southern highbush blueberry (*Vaccinium corymbosum*) variety. Its novelty lies in the following unique combination of features:

1. Has a low chilling requirement.
2. Produces a vigorous, upright bush.
3. Produces large, medium-blue berries with a small dry picking scar and high firmness.
4. Is capable of high yields of berries that ripen before May 20 in northeast Florida.

4 Drawing Sheets

Latin name of the genus and species: *Vaccinium corymbosum* L.
Variety denomination: 'Abundance'.

BACKGROUND OF THE INVENTION

Southern highbush blueberries are a relatively new type of cultivated blueberry. The cultivated varieties of southern highbush were developed by lowering the chilling requirement of northern highbush blueberry varieties, which were domesticated during the early 1900s from high-chill forms of *Vaccinium corymbosum* from Michigan and New Jersey. A native Florida blueberry species, *Vaccinium darrowi*, provided the low-chill genes needed to produce southern highbush blueberry. Southern highbush blueberries can be cultivated in areas with mild winters, where warm temperatures in late winter and early spring permit flowering and ripening early in the season. Southern highbush and northern highbush blueberry varieties are complementary; together they provide blueberries for the fresh market from April 1 to September 15 in the northern hemisphere and from October 1 to March 15 in the southern hemisphere.

To be commercially useful, southern highbush blueberry varieties require favorable combinations of numerous plant and berry characteristics. Plant characteristics include high vigor, low chilling requirement, high yield potential, and the ability to tolerate a dozen or more potentially serious diseases that thrive in hot, wet areas. Desirable berry qualities include large size, light blue color, and dry picking scar, along with good firmness, texture, and flavor.

'Abundance' came from a long-term breeding program at the University of Florida in which recurrent selection is being used to bring together as many desirable characteristics as possible in a series of varieties that are adapted to various parts of the southeastern United States. 'Abundance' came from a cross between FL93-70 (unpatented) and FL90-4 (unpatented), which was made in a greenhouse in Gainsville, Fla. in March 1993. The seedling was first fruited in a high-density nursery in Gainesville in April 1995. Plants were propagated from softwood cuttings and a 15-plant plot was established in a commercial blueberry planting at Windsor, Fla. (near Gainsville) in January 1999. The clone was repropagated and several hundred plants were planted in Archer, Fla. in January 2001. These plants were observed each year during fruiting season. The plants appear uniform in all characteristics, and the clone appears to have a combination of characteristics that would make it a valuable commercial cultivar.

BRIEF SUMMARY OF THE INVENTION

'Abundance' is a new southern highbush blueberry variety that has the following unique combination of characteristics that set it apart from other blueberry cultivars:

a. Produces a large, vigorous bush with a high yield capacity.
b. Produces a large berry, averaging 3.1 g per berry at the start of the season on vigorous plants.
c. Has berry color, scar, firmness, and flavor that are suitable for commercial production of bluberries for the fresh and frozen market.
d. Has a chilling requirement of about 300 hours below 7° C. per winter.
e. Ripens most of its fruit between April 20 and May 15 in northeast Florida.
f. 'Abundance' differs from its parents in many details as would be expected from a seedling from a cross between two highly heterozygous clones. Compared to parent FL93-70, the berry of 'Abundance' is lighter blue in color and has a better picking scar. Compared to parent FL90-4, which is rather short in stature and rounded in form, 'Abundance' is much more vigorous and upright in growth habit.

BRIEF DESCRIPTION OF THE DRAWING

The color chart used in this specification is "The Pantone Book of Color", by Leatrice Eiseman and Lawrence Herbert. 1990. Harry N. Abrams, Inc., Publishers, N.Y. Where colors in the drawings differ from the Pantone color designations in the verbal descriptions, the Pantone color designations are the more accurate.

DETAILED BOTANICAL DESCRIPTION

Market Class

Figure 1:
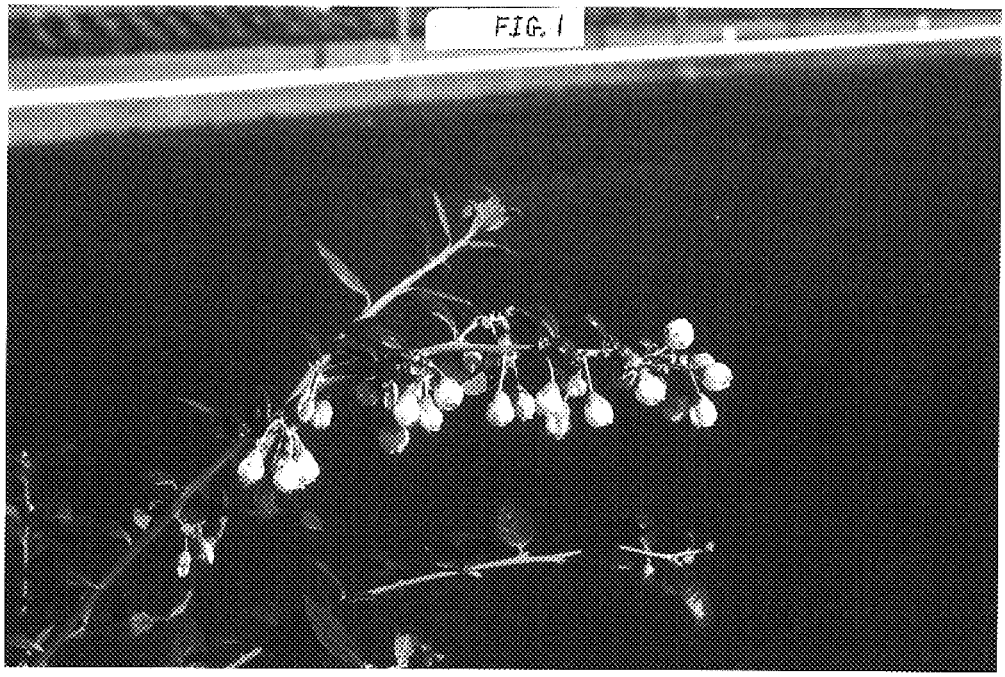
FIG. 1 shows flower clusters of 'Abundance' during February on young plants that were maintained evergreen in a greenhouse. This environment elongates the peduncles compared to what would be seen on field-grown plants that have been chilled before flowering. The white corollas and urceolate flowers are typical.
Figure 2:
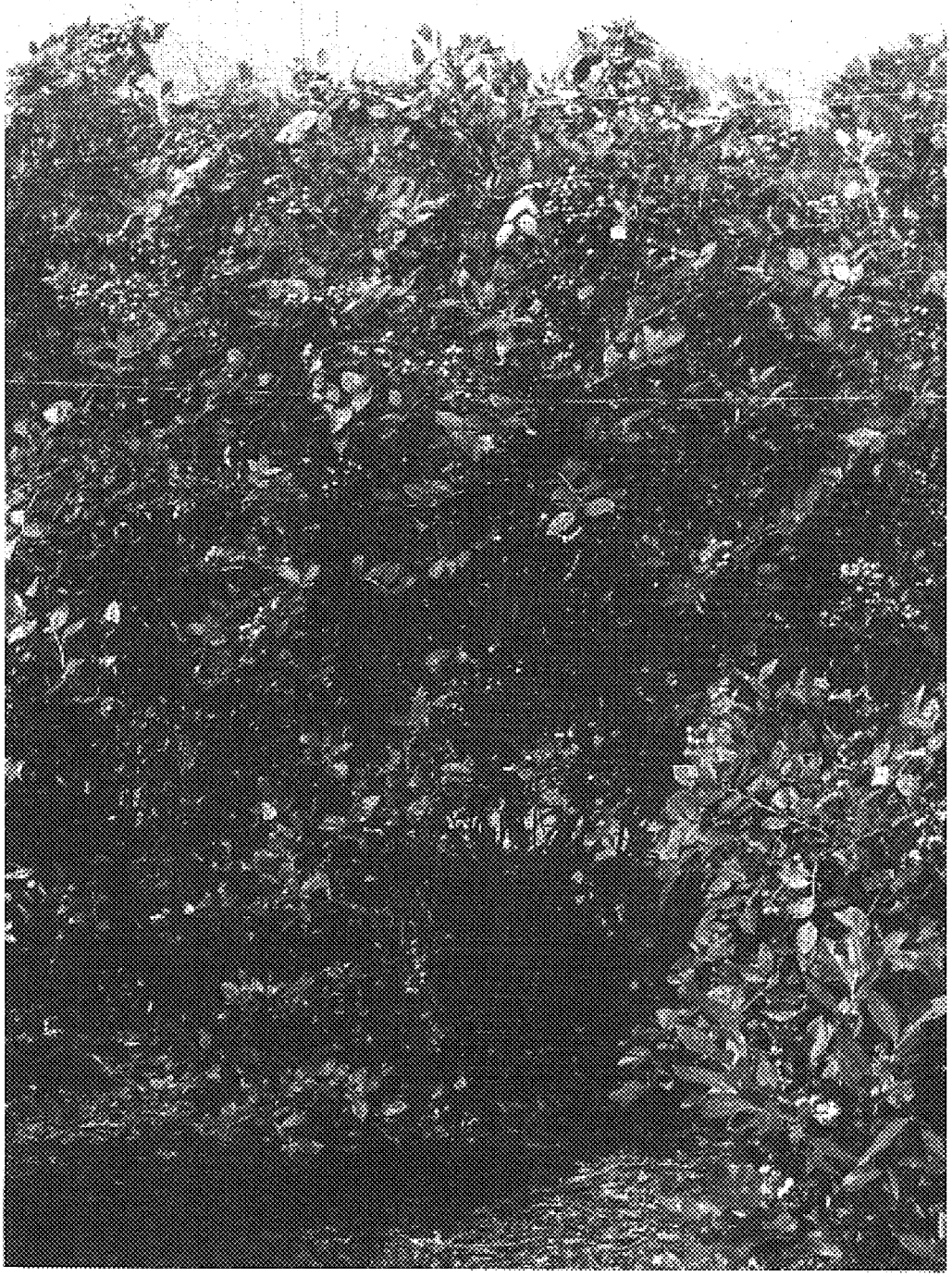
FIG. 2 shows a 4-year-old plant of Abundance in early May. The plant is about 2.5 m tall. The dense canopy and large fruit-bearing surface are characteristic.
Figure 3:
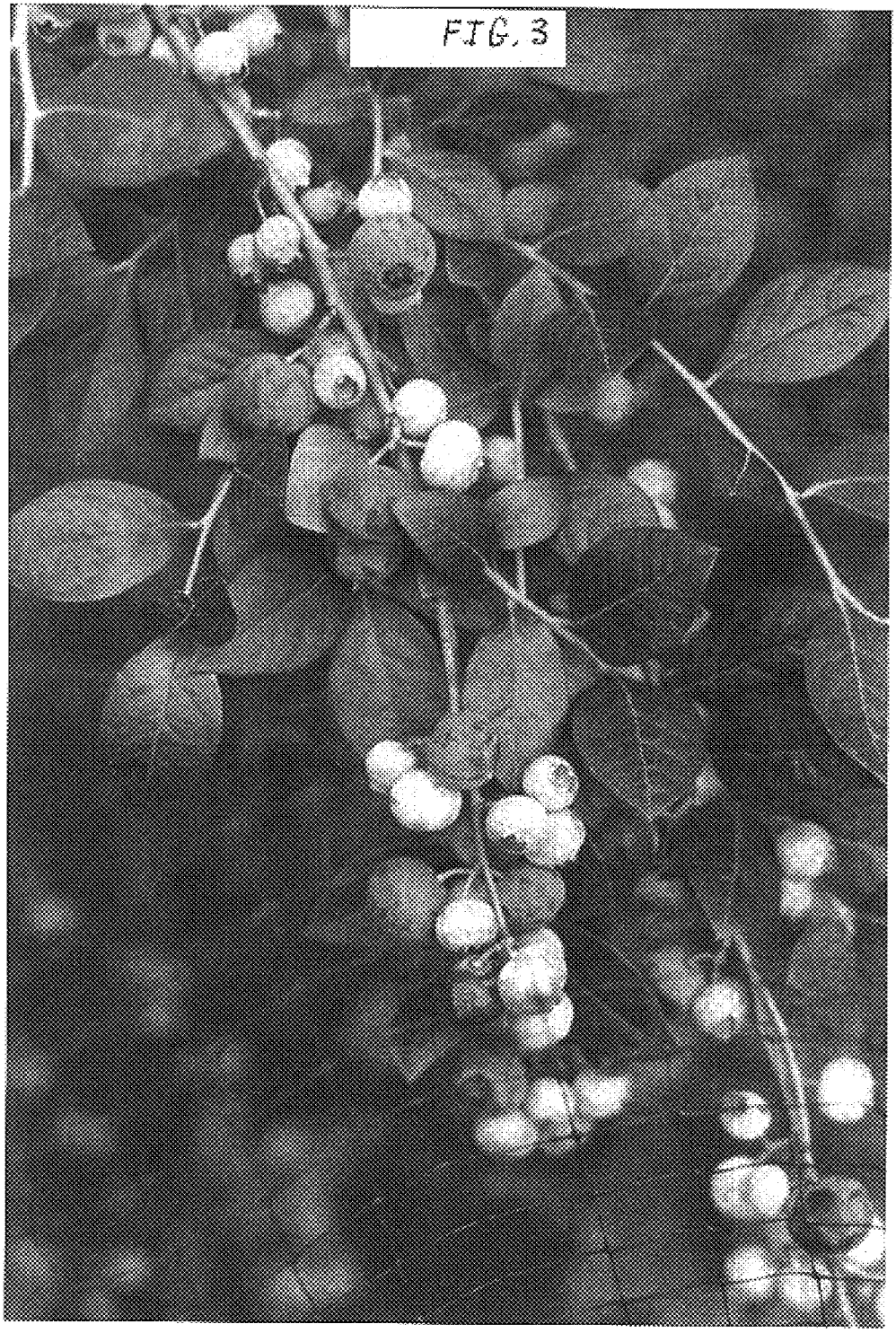
FIG. 3 shows at close range the long fruiting branches on a field-grown plant in late April. The dark green leaves and frosty-blue berries are typical.
Figure 4:
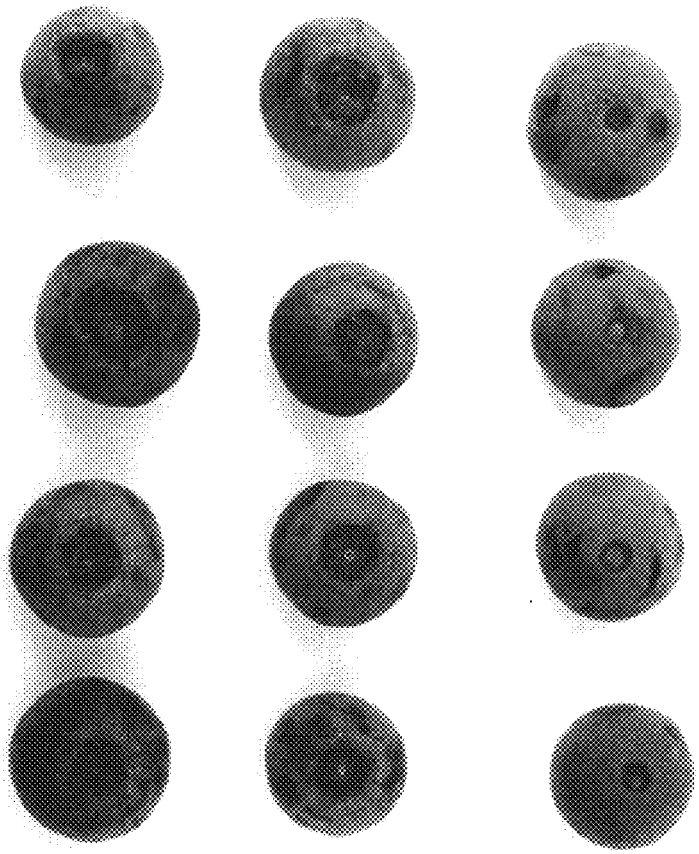
FIG. 4 shows, at close range, the mature berries. In the column to the right, the small to medium-size picking scar can be seen. In the two columns to the left, the calyx lobes, which sometimes take the form of a star, can be seen.

'Abundance' produces highbush blueberries suitable for both the fresh and processed fruit markets.

Bush

Plant charateristics were measured on 4-year-old plants in a commercial blueberry planting at Windsor in northeast Florida. The field had been irrigated, pruned, and managed in a way typical for commercial blueberry fields in the area.

Plant height: 2.5 m.

Canopy diameter measured at the widest part: 1.4 m.

Plant vigor: Very high.

Growth habit: Upright, with canes erect and sprouting from a narrow base.

Flower bud density (number): Very high.

Twigginess: Medium.

Tendency to remain evergreen in winter: Medium to low.

Truck and Branches

Suckering tendency: Medium; 12 to 15 major canes produced from a base 30 cm across.

Surface texture of strong, 6-month old stems observed August 18: Smooth.

Surface texture of 1-year-old wood observed August 18: Smooth, becoming rough due to vertical fissures filled with rough, corky bark.

Surface texture of 3-year-old and older wood surface: Rough, but becoming smoother in large canes over 3 years old.

Color of vigorous, 6-month-old shoots on August 18: 'Beechnut' (Pantone 14-0425).

Color of 1-year-old bark: 'Copper' (Pantone 16-1325).

Color of 3-year-old rough-textured canes: 'Oyster white' (Pantone 13-1007).

Internode length on strong, upright shoots measured August 18: 17 mm.

Leaves

Leaf length including petiole, from tip of petiole to end of blade: Mean=66 mm.

Leaf width, widest point: 33 mm.

Leaf shape: Oval. Midrib terminates in a dew tip, about 0.5 mm long, visible under 15 X microscope.

Leaf margin: Minutely serrate.

Color of upper surface of leaves: 'Grasshopper' (Pantone 18-0332).

Color of lower surface of leaves: 'Sage' (Pantone 16-0421).

Pubescence, upper surface of leaves: Numerous short, white, curved hairs on the midrib and major veins.

Pubescence, lower surface of leaves: Numerous short, white, curved hairs on the midrib and major veins.

Pubescence, leaf margins: A few short, white hairs along margin. Round, sessile glands along the margin of the leaf, at positions corresponding to invaginations of the serrate leaf margin.

Relative time of leafing and flowering in spring: Flower buds and leaf buds sprout at about the same time.

Flowers

Flower arrangement: Flowers are arranged alternately along a short, leafless, deciduous branch.

Flower fragrance: Light honeysuckle fragrance if newly opened flowers are harvested and stored in a closed container for 15 minutes.

Pedicel length at time of anthesis: 4 mm.

Peduncle length at time of anthesis: Variable. Averages 11 mm.

Petals: Fused into a corolla tube with 5 lobes.

Pollen staining: Approximately 99% of the pollen grains stain with acetocarmine dye, indicating that a high percentage of the pollen grains are well formed, starch filled, and potentially viable.

Pollen abundance: Dried flowers shed pollen in great abundance.

Pollen color: 'Golden rod', Pantone 14-0951.

Flower type: Perfect, ovary inferior, petals fused into a corolla tube, the 10 stamens inserted at the base of the corolla tube.

Flower length from pedicel attachment point to corolla tip: 12 mm.

Length of corolla tube: 9 mm.

Style length from top of ovary to stigma tip: 10 mm.

Calyx diameter at anthesis from tip of one lobe to tip of the opposite lobe: 6 mm.

Diameter of corolla tube at widest point: 8 mm.

Corolla aperture diameter: 4 mm.

Corolla surface texture: Smooth.

Flower shape: Urceolate.

Corolla color at anthesis: White — the color of the unprinted spaces in the Pantone Book of Color.

Style color at anthesis: 'Bright chartreuse', Pantone 14-0445.

Pedicel and peduncle color: 'Apple green', Pantone 15-0543.

Flowering period: Average date when first 50% of the flowers open at Gainsville, Fla. is February 18. This compares with the following dates for some other varieties: 'Emerald' (U.S. Plant Pat. No. 12,165): February 20; 'Jewel' (U.S. Plant Pat. No. 11,807): February 20; Millenia (U.S. Plant Pat. No. 12,816): February 19; Star (U.S. Plant Pat. No. 10,675): March 2.

Flower cluster (tight, medium, or open): Medium.

Average number of flowers per cluster: 4.

Location of tip of stigma relative to the lip of the corolla: Tip of the stigma extends equally far as the tips of the corolla lobes.

Distance between the stigma tip and the part of the anther pore nearest the stigma tip: 2.4 mm.

Berry

Mean date of first commercial harvest (25% of berries ripe): April 30 at Windsor, Fla.

Mean date of last harvest: May 20 at Windsor, Fla.

Diameter of calyx aperture on mature berry: 6.6 mm.

Calyx lobes on mature berry: Small and inconspicuous.

Berry cluster: (tight, medium, or loose): Loose.

Pedicel length on ripe berry: 6.7 mm.

Peduncle length at the time berries are ripe: Mean 10.9 mm but highly variable.

Number of berries per cluster: Mostly 5 to 6.

Detachment force for ripe berry: Medium. Ripe berries can be harvested rapidly by hand.

Berry weight: Means 3.1 g per berry for first part of crop on vigorous, well-pruned plants.

Berry height: 14.3 mm.

Berry width: 18.1 mm.

Color of the surface of the mature berry on the plant: 'Vapor blue' (Pantone 14-4203).

Color of the surface of the mature berry after harvest and packing: 'Steel gray' (Pantone 18-4005).

Color of the surface of the mature berry after polishing: Shiny black.

Berry surface wax: Medium in amount and medium in persistence when the berry is handled.

Mature berry internal flesh color: 'Oyster white' (Pantone 13-1007).

Pedicel scar: Small and dry. A few skin tears if berries are not harvested promptly at maturity.

Berry firmness: High.

Berry flavor: Excellent; sweet and slightly acid.

Berry texture: Good; small seeds and thin skins.

Color of dried seeds: 'Brown sugar' (Pantone 17-1134).

Weight of well-developed seeds: 0.66 mg.

Length of well-developed seeds: 1.5 mm.

Width of well-developed seeds: 0.9 mm.

Physiological Characteristics

Chilling requirement: About 300 hours per winter below 7° C.

Cold hardiness: Flowers and fruit hardy to −3° C. The plant, during winter dormancy, is hardy to −15° C.

Productivity: Because of its high vigor, large bush size, and prolific flower bud formation, 'Abundance' is capable of high yields. Yields on 5-year-old plants at Windsor, Fla. have averaged 5 to 7 pounds of fruit per plant per year.

Ease of propagation: 'Abundance' is easy to propagate from softwood cuttings. Several thousand plants have been asexually propagated in Gainsville, Fla. by this method, and all appear to reproduce the variety exactly.

Diseases, Insects, Mites

Phytophthora root rot: Resistance to this disease appears to be about average for southern highbush blueberry varieties. 'Abundance' should only be planted on well-drained soils.

Stem blight (*Botryosphaeria dothidia*): Resistance appears to be average for southern highbush blueberry varieties.

Cane canker (*Botryosphaeria corticis*): Plants appear to have good resistance to common races.

Fungal leaf spots (various pathogens): Appears to be about average for southern highbush varieties. Fungicidal sprays will be required in commercial plantings in humid climates to maximize yields.

Overall survival in the field: Medium to high.

It is claimed:

1. A new and distinct southern highbush blueberry plant, substantially as illustrated and described, characterized by having a vigorous, highly productive bush, a large, high-quality berry, and a low chilling requirement.

* * * * *